United States Patent [19]
Guest

[11] Patent Number: 5,404,764
[45] Date of Patent: Apr. 11, 1995

[54] LIQUID SAMPLE CONTAINER SYSTEM

[76] Inventor: Rodger L. Guest, 59 S. Beechwood Rd., Bedford Hills, N.Y. 10507

[21] Appl. No.: 192,350

[22] Filed: Feb. 7, 1994

[51] Int. Cl.⁶ .............................................. G01N 1/02
[52] U.S. Cl. ..................................... 73/864; 435/292; 435/295; 366/242; 366/306
[58] Field of Search .................... 73/863, 863.23, 864, 73/864.51, 864.72, 864.91; 128/760, 762; 435/292, 294, 295; 366/241, 242, 261, 306

[56] References Cited

U.S. PATENT DOCUMENTS

| | | | |
|---|---|---|---|
| 709,858 | 9/1902 | Arthurs | 73/864.51 |
| 3,368,549 | 2/1968 | Barr et al. | 435/295 |
| 3,849,256 | 11/1974 | Linder | 195/139 |
| 4,559,837 | 12/1985 | Cerqueier | 73/864.44 |
| 4,624,929 | 11/1986 | Ullman | 436/179 |
| 4,803,998 | 2/1989 | Kezes et al. | 435/295 |
| 4,982,615 | 1/1991 | Sulran et al. | 73/864.8 |

*Primary Examiner*—Richard E. Chilcot, Jr.
*Assistant Examiner*—Eric S. McCall
*Attorney, Agent, or Firm*—David L. Baker; Rhodes & Ascolillo

[57] ABSTRACT

A liquid sample container system is for receiving and protecting a liquid sample including oil obtained from a surface of a large liquid source having at least a thin layer of oil thereon. A cylindrical jar of the container system has a bottom, an open top and a height therebetween. The jar has an uncontaminated interior for receiving the liquid sample therein by gravity toward the bottom. The jar has threads about the open top. The jar lid has an inside and matching threads for being threadably received on the threads of the jar for sealing the interior thereof. A lid insert has an outer surface of polytetrafluoethylene to which oil tends to temporarily adhere. The lid insert has a disc portion located within the inside of the jar lid for being disposed over the open top when the jar lid is threadably installed on the jar. The lid insert has an extended portion extending perpendicular from the disc portion away from the jar lid for being deposited within the interior of the jar lid when the jar lid is installed thereon.

9 Claims, 2 Drawing Sheets

LIQUID SAMPLE CONTAINER SYSTEM

BACKGROUND OF THE INVENTION

1. Field of the Invention

The present invention relates to a liquid sample container system for receiving and protecting an uncontaminated liquid sample therein. It is particularly configured for such a liquid sample including oil obtained from the surface of a large liquid sample having at least a thin layer of oil thereon.

2. Description of the Related Art

Typically, when attempting to obtain a sample of oil from the surface of water or the like, the sample jar is tilted to skim a portion of the sample from the surface of the water. After a liquid sample including both the oil and water is obtained, the jar is typically inverted and the cap loosened to allow the water to drain out. The process must be repeated until a sufficient amount of oil is obtained for the sample.

Throughout such a process, it is not uncommon for the sampler to be wearing gloves. However, even with the use of such gloves, the collection system as described often results in the sample being contaminated. Such a means for collecting a sample of oil can be time consuming, troublesome, messy, and susceptible to contamination.

A number of sample container systems have heretofore been provided but are typically configured to collect and protect a sample of a particular material under a particular environmental condition.

For example, U.S. Pat. No. 4,982,615 discloses a sterile container for collecting biological samples for the purposes of analysis. U.S. Pat. No. 4,007,639 is directed to a capillary vessel for blood removal which includes a nozzle of capillary diameter, with a remaining portion widened of size such that a micro pipette can be inserted therein with the end of the nozzle being closed with a plug. U.S. Pat. No. 4,624,929 is directed to a device for collecting liquid sample wherein the device is adapted for use with a container having a volume of liquid for diluting the liquid sample. Finally, U.S. Pat. No. 3,849,256 discloses a device for use in (and a method of) testing urine, and comprises a casing having a removable lid and a hollow testing column disposed within the casing. The testing column has a number of test fields which are spaced apart from each other.

SUMMARY OF THE INVENTION

None of the sample systems discussed hereinabove are particularly adapted for collecting a liquid sample from a large liquid source, particularly when trying to obtain a sample of oil in a thin layer on the surface of a large liquid source.

It is an object of the present invention to provide a liquid sample container system which may be conveniently and reliably employed to obtain a sample of oil from the surface of water.

It is another object of the invention to provide such a liquid sample container system which is simple to employ and inexpensive to provide.

It is a further object of the invention to provide such a liquid sample container system which is not messy and will not result in the contamination of the sample.

These and other objects of the invention are provided in a preferred embodiment thereof including a liquid sample container for receiving and protecting an uncontaminated liquid sample therein. The liquid sample container system includes a hollow container having a bottom, an open top and a height therebetween. The container has an uncontaminated interior for receiving the liquid sample therein by gravity toward the bottom. A container lid is adapted to be removably installed on the container for sealing the open top. The container lid has an outside and an inside with the inside for being disposed toward the interior when the container lid is installed on the container for sealing the open top. The container lid has an extension joined to the inside for insertion into the interior when the container lid is installed on the container for sealing the open top. The inside and the extension have a polytetrafluoethylene surface.

In one aspect, the invention includes the container having a threaded region at the open top and the container lid including a threaded portion for being received on the threaded region of the container. The preferred extension has a length from the inside and the length is at least one half of and less than the height of the container. The preferred extension is planar and is disposed generally perpendicular to the inside of the container lid.

In another aspect of the invention, the extension includes an extended end remote from the inside of the container lid which is shaped in the form of a spoon or ladle. The outside of the container lid may include a means for attaching a support line thereto for lowering the container lid to a remote location.

In another aspect of the invention, the liquid sample container system can include an extension having an irregular surface. The irregular surface may include a plurality of surface cavities.

In yet another aspect of the invention, a liquid sample container system is provided for receiving and protecting a liquid sample including oil obtained from a surface of a large liquid source having at least a thin layer of the oil thereon. The liquid sample container includes a cylindrical jar having a bottom and an open top and a height therebetween. The jar has an uncontaminated interior for receiving the liquid sample therein by gravity toward the bottom. The jar has threads about the open top. A jar lid has an inside and matching threads for being threadably received on the threads of the jar for sealing the interior thereof. A lid insert has an outer surface with an oil adhering surface material thereon to which the oil tends to temporarily adhere. The lid insert has a disc portion located within the inside of the jar lid for being disposed over the open top when the jar lid is threadably installed on the jar. The lid insert has an extended portion extending perpendicularly from the disc portion away from the jar lid for beingdisposed within the interior of the jar when the jar lid is installed thereon. Accordingly, the liquid sample container system is configured so that the extended portion can be repeatedly inserted into the surface of the large liquid source for temporary collection of a portion of the liquid sample thereon. The extended portion will then be repeatedly extended into the interior of the jar and shaked to cause the portion of the liquid sample temporarily collected thereon to be separated therefrom from being received within the interior of the jar until the desired liquid sample is obtained and the jar is sealed by the jar lid.

In the preferred liquid sample container system, the oil adhering surface material is polytetrafluoethylene. The extended portion has a length from the disc portion and the length is at least one half of and less than the height of the jar. The preferred extended portion is planar.

In yet another aspect, the invention includes an extended portion in the shape of a spoon or ladle which is disposed generally parallel with the disc portion for being dipped into the large liquid source for collection of the portion of the liquid sample therein. The jar lid may include an outside surface and the outside surface may include an extended loop for attaching a supporting line thereto.

In another aspect of the invention, an extended portion may be irregular in shape and could have a sponge-like shape.

DESCRIPTION OF THE PREFERRED EMBODIMENT

Figure 1:
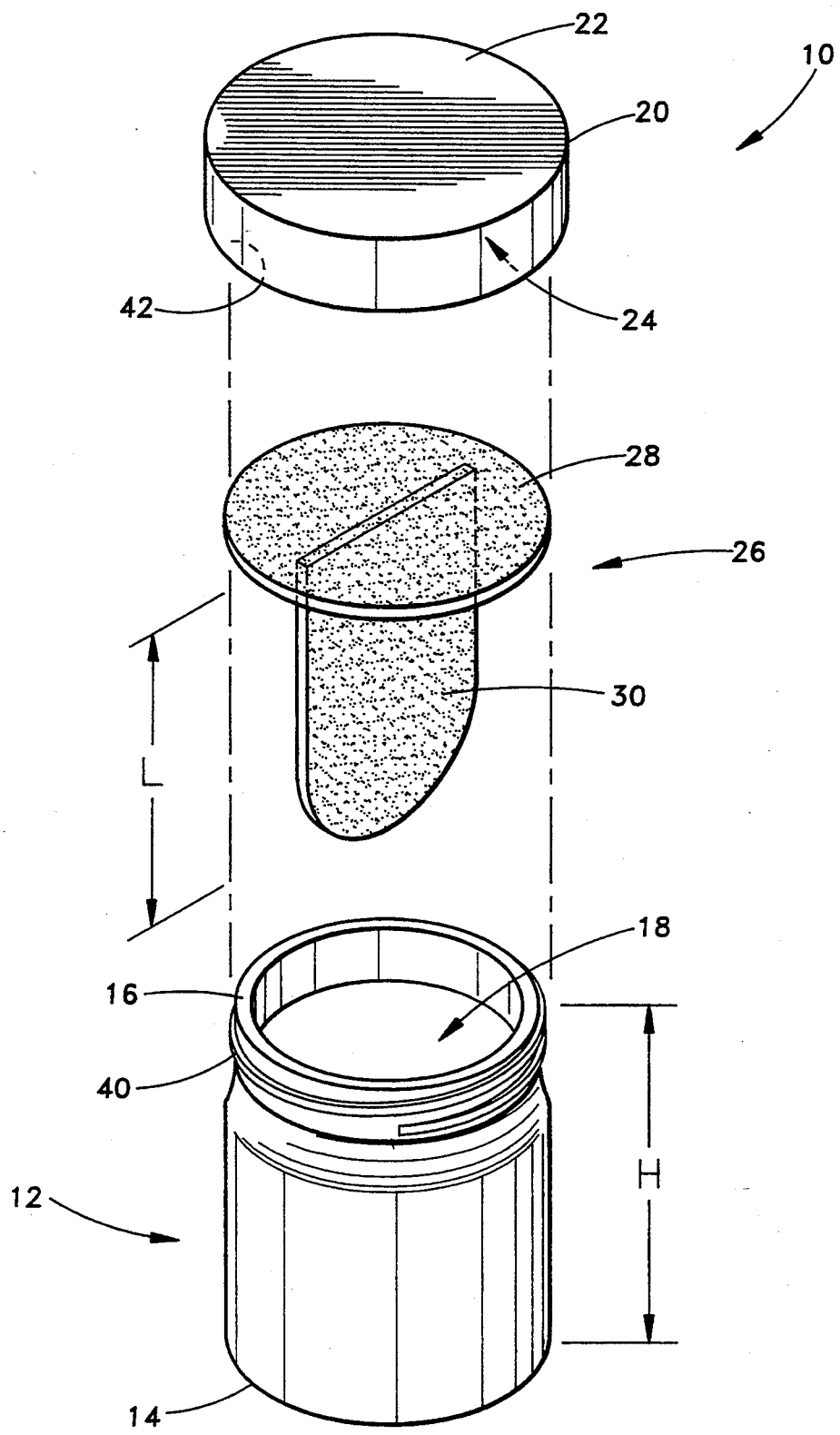
FIG. 1 is an exploded perspective view of a preferred liquid sample container system including various features of the invention.

As seen in FIG. 1, a preferred liquid sample container system 10 includes a hollow container 12 having a bottom 14, an open top 16 and a height H therebetween. The container 12 has an uncontaminated interior 18 for receiving the liquid sample therein by gravity toward the bottom 14. A container lid 20 is adapted to be removably installed on the container 12 for sealing the open top 16. The container lid 20 has an outside 22 and an inside 24 for being disposed toward the interior 18 when the container lid 20 is installed on the container 12 for sealing the open top 16. A lid insert 26 is installed against the inside 24 of the container lid 20. The lid insert 26 of the preferred liquid sample container system 10 includes a disc portion 28 which is adapted to be disposed over the open top 16 when the lid 24 is installed on the container 12. The lid insert 26 further includes an extension 30 from the disc portion 28 which is adapted to be inserted into the interior 18 of the container 12 when the container lid 20 is installed on the container 12 for sealing the open top 16. The liquid sample container system 10 includes the lid insert 26 having a surface material having characteristics to which oil tends to temporarily adhere. Preferably, the lid insert 26 includes a surface material of polytetrafluoethylene which has been found to be particularly attractive for the collection of an oil sample thereon.

The preferred container 12 is a four ounce, large mouth glass jar which includes a threaded region 40 around the open top 16 which is adapted to mate with and receive internal threads 42 on the inside of the container lid 20. As mentioned above, the preferred liquid sample container system 10 is intended to have the lid 20 directed toward the liquid source so that the extension 30 can be repeatedly dipped into the liquid source of water or the like having a thin layer of oil thereon which is intended to be collected for analysis. Consequently, the extension 30 preferably includes a length L which is at least one half of, and less than, the height H of the container 12.

Typically, the preferred liquid sample container system 10 will be employed as the sampler repeatedly inserts the extension 30 into the surface of the large liquid source for temporarily collecting a portion of the liquid sample, including the oil, thereon. The polytetrafluoethylene surface has been found to cause a quantity of the oil to generally adhere thereon until the lid 20 and insert 26 are directed toward the interior 18 of the container 12. When properly aligned, the lid 20 is shaked or tapped to cause the portion of the liquid sample temporarily collected thereon to be separated therefrom for being received from the interior of the container. These steps are repeated until a sufficient liquid sample is obtained and the container is sealed by the container lid. Although some water might also be on the surface of the extension 30 after each dip into the liquid source, the relative quantity of oil is sufficient to insure the desired amount can be collected for a sample.

As thus described, a sampler can conveniently collect oil from the surface of water without the use of gloves, without contaminating the sample, and without producing a messy exterior on the container 12 as frequently occurred during the sample collection method discussed hereinabove.

Figure 2:
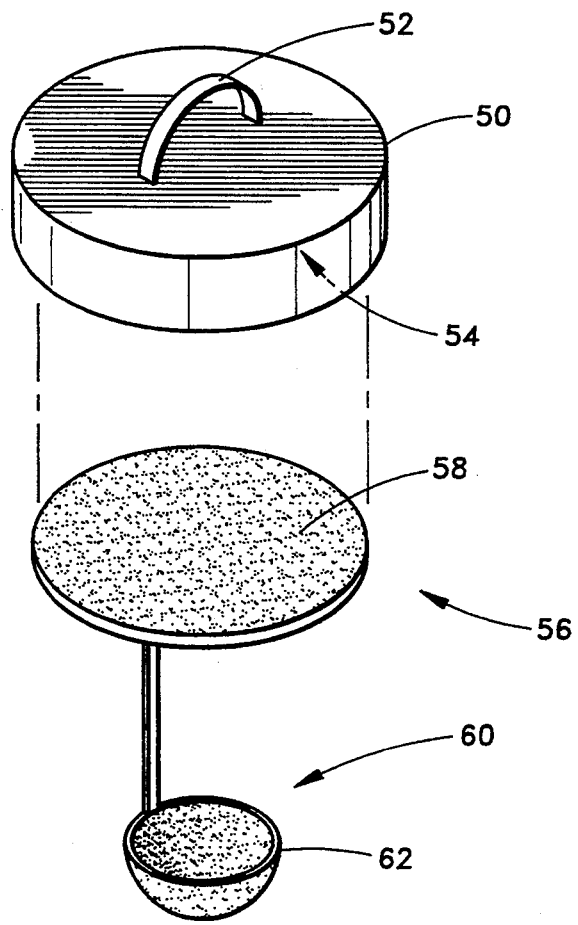
FIG. 2 is an exploded perspective view of an alternative lid and lid insert of an alternative liquid sample container system including various features of the invention.

The preferred extension 30 of the liquid sample container system 10 of FIG. 1 is generally planar, extending generally perpendicular from the disc portion 28 and can be conveniently used to obtain an oil sample from a surface of a source of water which is easily accessible. However, there are occasions when such a liquid sample container system may be employed to obtain a sample of oil from the surface of water which is generally inaccessible. For example, it is often desirable to obtain a source of oil from water located in a sewer pipe. Accordingly, as seen in FIG. 2, an alternative container lid 50 is similar to the container lid 20 but includes an upperly extending loop 52 on the outer surface thereof. The loop 52 provides means for attaching a drop line or the like (not shown) for lowering the lid 50 toward the surface of water having oil thereon in an inaccessible place such as a sewer pipe. An alternative insert 56 includes a disc portion 58 similar to the disc portion 28 for receipt within an inside 54 of the container lid 50. However, an alternative extension 60 includes a spoon or ladle means 62 on a lower end thereof which is disposed generally parallel to the disc portion 58. The spoon or ladle means 62 can be dipped into the liquid source to allow any surface oil thereon to be collected therein. The drop line (not shown) would allow the lid 50 and sample within the spoon or ladle means 62 to be withdrawn from the surface of the liquid source and then inserted into the interior 18 of a container 12. Again, the oil within and on the spoon or ladle means 62 will be repeatedly shaked therefrom and deposited within the uncontaminated interior 18 of the container 12 until a sufficient sample is obtained.

Figure 3:
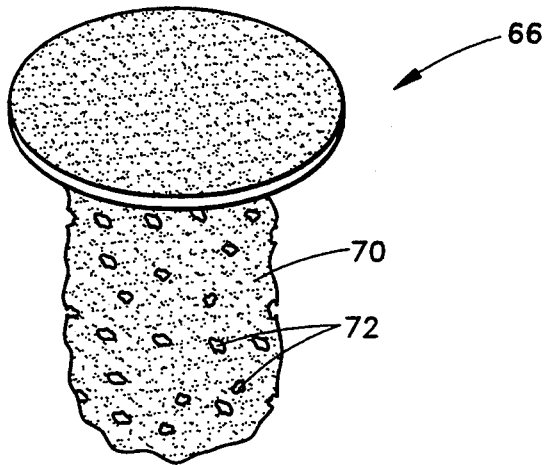
FIG. 3 is a perspective view of an alternative lid insert of an alternative liquid sample container system including various features of the invention.

As seen in FIG. 3, another alternative lid insert 66, which would be employed in the same manner as the lid insert 26 of FIG. 1, includes an extension 70 having an irregular shape. The irregular shape may be generally sponge shaped and might, for example, include a plurality of surface cavities 72 thereon. Such an irregular shape might allow a greater quantity of oil to be collected on the surface thereof so that less steps may be required until a sufficient sample is obtained within the interior 18 of the container 12.

While the liquid sample container systems disclosed herein include features which are particularly adapted for the collection of oil from a thin later on the surface of a liquid source, it should be clear to those skilled in the art that some of the features may be varied without departing from the scope of the invention as claimed. Clearly, other alternatives may be made to the liquid sample container system while still providing the desired means for obtaining a sample in the manner described. Consequently, while the invention has been herein described by way of particular preferred embodiments, various substitutions of equivalents may be affected without departing from the spirit and scope of the invention as set forth in the following claims.

What is claimed is:

1. A liquid sample container system for receiving and protecting an uncontaminated liquid sample therein, comprising:

a hollow container having a bottom, an open top, and a height therebetween;

said container having a uncontaminated interior area for receiving the liquid sample therein by gravity toward said bottom;

a container lid adapted to be removably installed on said container for sealing said open top;

said container lid having an outside surface and an inside surface with said inside surface being disposed toward said interior area when said container lid is installed on said container for sealing said open top;

said container lid having an extension member joined to said inside surface for insertion into said interior when said container lid is installed on said container for sealing said open top; and said inside surface and said extension member having a polytetrafluoethylene surface.

2. The liquid sample container system according to claim 1, wherein said container includes a threaded region at said open top and said container lid includes a threaded portion for being received on said threaded region of said container.

3. The liquid sample container system according to claim 1, wherein said extension member has a length from said inside surface and said length is at least one-half of and less than said height.

4. The liquid sample container system according to claim 1, wherein said extension member is planar and is disposed generally perpendicular to said inside surface of said container lid.

5. The liquid sample container system according to claim 1, wherein said extension member includes an extended end remote from said inside surface of said container lid and said extended end includes spoon means.

6. The liquid sample container system according to claim 1, wherein said outside surface of said container lid includes attaching means for supporting line means thereto.

7. The liquid sample container system according to claim 1, wherein said extension has an irregular shape.

8. The liquid sample container system according to claim 7, wherein said extension member includes a plurality of surface cavities.

9. A liquid sample container system for receiving and protecting a liquid sample, including oil obtained from a surface of a large liquid source having at least a thin layer of the oil thereon, comprising:

a cylindrical jar having a bottom, an open top, and a height therebetween;

said jar having an uncontaminated interior area for receiving said liquid sample therein by gravity toward said bottom;

said jar having threads about said open top;

a jar lid having an inside and matching threads for being threadably received on said threads of said jar for sealing the interior thereof;

a lid insert having an outer surface with an oil adhering surface material thereon to which the oil tends to temporarily adhere, wherein said oil adhering surface material is polytetrafluroethylene.

said lid insert having a disc portion located within said inside of said jar lid being disposed over said open top when said jar lid is threadably installed on said jar; and said lid insert having an extended portion extending perpendicularly from said disc portion away from said jar lid for being disposed within said interior area of said jar when said jar lid is installed thereon, whereby said extended portion is for being repeatedly inserted into the surface of the large liquid source for temporary collection of a portion of the liquid extended into said interior area of said jar and shaked to cause the portion of the liquid sample temporarily collected thereon to be separated therefrom for being received within said interior area of said jar until the liquid sample is obtained and said jar is sealed by said jar lid.

* * * * *